US005972683A

United States Patent [19]
Tsai

[11] Patent Number: 5,972,683
[45] Date of Patent: Oct. 26, 1999

[54] MUTANT TYPE SUBTILISIN YAB AND ITS APPLICATION

[75] Inventor: Ying-Chieh Tsai, Taipei, Taiwan

[73] Assignee: National Science Council, Taipei, Taiwan

[21] Appl. No.: 09/135,658

[22] Filed: Aug. 18, 1998

[30] Foreign Application Priority Data

Sep. 4, 1997 [TW] Taiwan .................................. 86112766

[51] Int. Cl.$^6$ .............................. C12N 9/54; C12N 15/57; C12N 15/75; C12S 3/00

[52] U.S. Cl. ......................... 435/221; 435/69.1; 435/220; 435/252.31; 435/320.1; 435/471; 435/267; 536/23.2

[58] Field of Search ..................................... 435/220, 221, 435/69.1, 471, 252.31, 320.1, 267; 536/23.2

[56] References Cited

U.S. PATENT DOCUMENTS

| | | | |
|---|---|---|---|
| 4,600,589 | 7/1986 | Robbins et al. | 426/56 |
| 5,700,676 | 12/1997 | Bott et al. | 435/221 |
| 5,709,901 | 1/1998 | Okisaka et al. | 426/611 |
| 5,780,285 | 7/1998 | Ballinger et al. | 435/222 |
| 5,846,802 | 12/1998 | Buxton et al. | 435/225 |

OTHER PUBLICATIONS

Gros et al., 1989, "Molecular dynamics refinement of a thermitase–elgin–c complex at 1.98 Å resolution and comparison of two crystal forms that differ in calcium content", *J. Mol. Biol.* 210:347–367.

Heinz et al., 1991, "Refined crystal structures of subtilisin novo in complex with wild–type and two mutant eglins", *J. Mol. Biol.* 217:353–371.

Kaneko et al., 1989, "Molecular cloning of the structural gene for alkaline elastase YaB, a new subtilisin produced by an alkalophilic *Bacillus* strain", *J. Bacteriol.* 171:5232–5236.

McPhalen & James, 1988, "Structural comparison of two serine proteinase–protein inhibitor complexes:Eglin–C–subtilisin carlsberg and CI–2–subtilisin novo", *Biochem.* 27:6582–6598.

Siezen et al., 1991, "Homology modelling and protein engineering strategy of subtilases, the family of subtilisin–like serine proteinases", *Protein Eng.* 4:719–737.

Takagi et al., 1992, "Effects of an alkaline elastase from an alkalophilic *Bacillus* strain on the tenderization of beef meat", *J. Agric. Food Chem.* 40:2364–2368.

Teplyakov et al., 1990, "Crystal structure of thermitase at 1 4 Å resolution", *J. Mol. Biol.* 214:261–279.

Tsai et al., 1983, "A new alkaline elastase of an alkalophilic bacillus", *Biochem. Int'l.* 7:577–583.

Tsai et al., 1984, "Substrate specificity of a new alkaline elastase from an alkalophilic bacillus", *Biochem. Int'l.* 8:283–288.

Tsai et al., 1986, "Characterization of an alkaline elastase from alkalophilic *Bacillus* Ya–B", *Biochimica et Biophysica Acta* 883:439–447.

Tsai et al., 1988, "Production and further characterization of an alkaline elastase produced by alkalophilic *Bacillus* strain Ya–B", *Applied Environmental Microbiology* 54:3156–3161.

Tsai et al., 1988, "Specificity of alkaline elastase Bacillus of the oxidized insulin A– and B– chains", *J. Biochem.* 104:416–420.

*Primary Examiner*—Ponnathapura Achutamurthy
*Assistant Examiner*—William W. Moore
*Attorney, Agent, or Firm*—Pennie & Edmonds LLP

[57] ABSTRACT

The invention provides a group of subtilisin YaB mutants, which are obtained by the substitution of the glycine residues at the 124, 151 and 159 positions of wild type subtilisin YaB with other amino acid residues by site directed mutagenesis. The subtilisin YaB mutants have special substrate specificity and relatively higher elastin/casein hydrolyzing activity. The subtilisin YaB mutants can be used in various aspects such as the quality improvement of meat and the protein processing for foodstuff and feedstuff. Moreover, the invention also includes the nucleic acid sequences encoding such enzyme mutants and the uses of such enzyme mutants.

4 Claims, 2 Drawing Sheets

```
              1                  21                 41
YaB        ------QT-V---PWGINRVQAPIAQSRGFTGTGVRVAVLDTGI-SNHADL--RIRGGASFV
Carlsberg  ---AQT-V---PYGIPLIKADKVQAQGFKGANVKVQVLDTGIQASHPDL--NVVGGASFV
BPN'       ---AQS-V---PYGVSQIKAPALHSQGYTGSNVKVAVIDSGIDSSHPDL--KVAGGASMV
Thermitase YTPNDPYFSSRQYGPQKIQAPQAWDI-AEGSGAKIAIVDTGVQSNHPDLAGKVVGGWDFV 61                 81                101
PGEPNI-SDGNGHGTQVAGTIAALN-NSIGVLGVAPNVDLYGVKVLGASCSGSISGIAQGLQWAANNGMHIA
AGE-AYNTDGNGHGTHVAGTVAALD-NTTGVLGVAPSVSLYAVKVLNSSGSGSYSGIVSGIEWATTNGMDVI
PSETNPFQDNNSHGTHVAGTVAALN-NSIGVLGVAPSASLYAVKVLGADGSGQYSWIINGIEWAIANNMDVI
DNDSTP-QNGNGHGTHCAGIAAAVTNNSTGIAGTAPKASILAVRVLDNSGSGTWTAVANGITYAADQGAKVI 121                141                161                181
NNSLGSSAGSATMEQAVNQATASGVLVVAASGNSGA----GNVGFTARYANAMAVGATDQNNNRATFSQYGA
NMSLGGASGSTAMKQAVDNAYARGVVVVAAAGNSGNSGSTNTIGYPAKYDSVIAVGAVDSNSNRASFSSVGA
NMSLGGPSGSAALKAAVDKAVASGVVVVAAAGNEGTSGSSSTVGYPGKYPSVIAVGAVDSSNQRASFSSVGP
SLSLGGTVGNSGLQQAVNYAWNKGSVVVAAAGNAGN----TAPNYPAYYSNAIAVASTDQNDNKSSFSTYGS 201                221                241
GLDIVAPGVGVQSTVPGNGYASFNGTSMATPHVAGVAALVKQKNPSWSNVQIRNHLKNTATNL-GNTTQFGS
ELEVMAPGAGVYSTYPTNTYATLNGTSMASPHVAGAAALILSKHPNLSASQVRNRLSSTATYL-GSSFYYGK
ELDVMAPGVSIQSTLPGNKYGAYNGTSMASPHVAGAAALILSKHPNWTNTQVRSSLQNTTTKL-GDSFYYGK
VVDVAAPGSWIYSTYPTSTYASLSGTSMATPHVAGVAGLLAS-QG-RSASNIRAAIENTADKISGTGTYWAK

261
GLVNAEAATR
GLINVEAAAQ
GLINVQAAAQ
GRVNAYKAVQY
```

```
                1                        21                                 41
YaB         -----QT-V----PWGINRVQAPIAQSRGFTGTGVRVAVLDTGI-SNHADL--RIRGGASFV
Carlsberg   ---AQT-V----PYGIPLIKADKVQAGFKGANVKVAVLDTGIQASHPDL--NVVGGASFV
BPN'        ---AQS-V----PYGVSQIKAPALHSQGYTGSNVKVAVIDSGIDSSHPDL--KVAGGASMV
Thermitase  YTPNDPYFSSRQYGPQKIQAPQAWDI-AEGSGAKIAIVDTGVQSNHPDLAGKVVGGWDFV 61                                 81                          101
PGEPNI-SDGNGHGTQVAGTIAALN-NSIGVLGVAPNVDLYGVKVLGASGSGSISGIAQGLQWAANNGMHIA
AGE-AYNTDGNGHGTHVAGTVAALD-NTTGVLGVAPSVSLYAVKVLNSSGSGSYSGIVSGIEWATTNGMDVI
PSETNPFQDNNSHGTHVAGTVAALN-NSIGVLGVAPSASLYAVKVLGADGSGQYSWIINGIEWAIANNMDVI
DNDSTP-QNGNGHGTHCAGIAAAVTNNSTGIAGTAPKASILAVRVLDNSGSGTWTAVANGITYAADQGAKVI 121                       141                       161                       181
NNSLGSSAGSATMEQAVNQATASGVLVVAASGNSGA-----GNVGFTARYANAMAVGATDQNNNRATFSQYGA
NMSLGGASGSTAMKQAVDNAYARGVVVVAAAGNSGSTNTIGYPAKYDSVIAVGAVDSNSNRASFSSVGA
NMSLGGPSGSAALKAAVDKAVASGVVVVAAAGNEGTSGSSSTVGYPGKYPSVIAVGAVDSSNQRASFSSVGP
SLSLGGTVGNSGLQQAVNYAWNKGSVVVAAGNAGN----TAPNYPAYYSNAIAVASTDQNDNKSSFSTYGS 201                       221                       241
GLDIVAPGVGVQSTVPGNGYASFNGTSMATPHVAGVAALVKQKNPSWSNVQIRNHLKNTATNL-GNTTQFGS
ELEVMAPGAGVYSTYPTNTYATLNGTSMASPHVAGAAALILSKHPNLSASQVRNRLSSTATYL-GSSFYYGK
ELDVMAPGVSIQSTLPGNKYGAYNGTSMASPHVAGAAALILSKHPNWTNTQVRSSLQNTTKL-GDSFYYGK
VVDVAAPGSWIYSTYPTSTYASLSGTSMATPHVAGVAGLLAS-QG-RSASNIRAAIENTADKISGTGTYWAK

261
GLVNAEAATR
GLINVEAAAQ
GLINVQAAAQ
GRVNAYKAVQY
```

FIG. 2

MUTANT TYPE SUBTILISIN YAB AND ITS APPLICATION

FIELD OF INVENTION

The invention provides a group of subtilisin YaB mutants, nucleic acid sequences encoding such enzyme mutants, expression vectors containing such nucleic acid sequences, the preparation of such enzyme mutants and the uses thereof. The subtilisin YaB mutants of the invention have special substrate specificities that are substantially different from those of the wild-type subtilisin YaB and other subtilisins, and the relative elastin/casein hydrolyzing activities thereof are all substantially enhanced. Such protease mutants can be used in various aspects such as the quality improvement of meat and the protein processing for foodstuff and feedstuff.

BACKGROUND OF INVENTION

Elastin is a protein presented in the elastic fiber of the arteris, dermis etc. of vertebrates. Elastin has a large amount of special bridging structure such as desmosine and lysinonorleucin. The amino acid composition thereof is very special, with 50–60% of alanine and glycine. It is water-insoluble and cannot be easily hydrolyzed by ordinary proteases (Foster (1982) *Methods Enzymol.*, 82, 559–570; and Paz et al., (1982) *Methods Enzymol.*, 82, 571–587). Proteases capable of hydrolyzing elastin are specifically called as elastases, including porcine pancreatic elastase (Ardelt et al. (1970) *Biochim, Biophys. Acta*, 341, 318–326) and the proteases secreted by microorganisms such as *Pseudomonas aerugionsa* (Morihara et al. (1965) *J. Biol. Chem.*, 240, 3295–3304), Streptomyces griseus (Gertler et al (1971) *Eur. J. Biochem.*, 240, 3295–3304) and Flavobacterium sp. (Ozaki et al. (1975) *J. Biochem.*, 77, 171–180). It is generally considered that elastase is capable of hydrolyzing elastin as having (a) stronger binding affinity for elastin, and (b) stronger substrate specificity for alanine and glycine (Stone et al. (1982) *Methods Enzymol.*, 82, 588–605).

Bacillus sp. YaB is an aerobic gram positive bacterium. It is a rod-shaped bacillus capable of producing spores and it may form a yellow colony on the culture medium. The cell wall thereof contains D,L-diaminopimelic acid. The growth of the bacterium is better in the medium at pH 10 than under neutral environment. Bacillus sp. YaB has been deposited in the Food Industry Research and Development Institute (FIRDI), Hsin-Chu, Taiwan, under Accession No. CCRC 11751.

The enzyme of the invention, subtilisin YaB (also referred to hereinafter as protease YaB), is originally named as alkaline elastase YaB. It is an extracellular protease produced by alkalophilic Bacillus YaB. The enzyme has a molecular weight of about 27,000 and an isoelectric point of 10.6. The optimal reaction pH thereof is 11.75. It is highly hydrolytic for elastin and is therefore originally named as elastase YaB. Moreover, it is also substantially more hydrolytic for collagen than other subtilisin proteases. See, Tsai et al. (1983) *Biochem. Int.*, 7, 577–583; Tsai et al. (1984) *Biochem. Int.*, 8, 283–288; Tsai et al. (1986) *Biochim. Biophys. Acta*, 883, 439–447; Tsai et al. (1988a) *Appl. Environ. Microbiol.*, 54, 3156–3161; and Tsai et al. (1988b) *J. Biochem.*, 104, 46–420.

The high hydrolyzing activity of the enzyme for elastin can be demonstrated by its binding affinity to elastin and its enzyme-substrate specificity. Within the pH range lower than its isoelectric point, the enzyme has a very high binding affinity to elastin. At pH 7.0, after mixing 50 mg of the enzyme with 5 mg elastin, more than 60% of the protease YaB are bound to the elastin. Under the same conditions, only 60% of subtilisin BPN' and 5% of chymotrypsin are bonded. See, Tsai et al. (1986) *Biochim. Biophys. Acta*, 883, 439–447. With respect to substrate specificity, it is for large aromatic amino acids such as tyrosine and phenylalanine for typical subtilisins. However, the subject enzyme of the invention has the substrate specificity for small amino acids such as alanine and glycine, which meets to the characteristics of elastase. See, Tsai et al. (1984) *Biochem. Int.*, 8, 283–288.

The gene of the above enzyme has been cloned in *E. coli* and can be expressed in Bacillus. The nucleotide sequence of the gene has also been determined. See, Kaneko et al. (1989) *J Bacteriol.*, 171, 5232–5236. The primary structure of the enzyme deduced from the nucleotide sequence shows about 60% homology with other subtilisins, including subtilisin BPN', Carlsberg and the like. Therefore, the enzyme should be a member of the subtilisin family and its name should be changed to subtilisin YaB. This enzyme has distinctive characteristics among subtilisins. In addition to the aforementioned substrate specificity for small amino acids, the optimal reaction pH of the enzyme is 11.75, while the optimal reaction pHs of typical subtilisins are all between about 9.0 to 10.5.

With respect to the applications, the enzyme has the full potential to be developed to a meat tenderizing enzyme (Takagi et al. (1992) *J. Agric. Food Chem.*, 40, 2364–2368). Typical meats such as beef, pork and chicken all have connective tissues containing large amounts of hard proteins such as elastin and collagen. Commercially available meat tenderizers contain plant proteases such as papain and bromelain for hydrolyzing those hard proteins so as to increase the tenderness of meats. However, the substrate specificities of these protease are too low. In addition to elastin and collagen, myofibrillar proteins such as actin and myosin may also be hydrolyzed. Therefore, the taste of meats will be deteriorated. The enzyme of the invention has the substrate specificity that is substantially higher than those of these proteases such as papain. When used in the treatment of meats, the enzyme can hydrolyze the elastin and collagen contained in the meat while only exert little hydrolyzing activity on actin and myosin. The treatment of meat with the enzyme of the invention result in good taste.

However, because the substrate specificity of the currently available protease YaB is still not sufficiently strict, it is difficult to control the conditions for the treatment of meat. If the administration concentrate of the enzyme is too high in parts of the meat, the taste of meat may still be deteriorated. Therefore, it is still desired in the art to obtain a protease with even higher substrate specificity for hard proteins such as elastin and collagen, in particular those with little, even no activity for myofibrillar proteins such as actin and myosin.

None of the above background references has disclosed or suggested that the substrate specificity of subtilisin YaB can be enhanced and/or altered by protein engineering techniques, so as to enhance the efficacies of the enzyme in its known applications and/or to develop other new applications.

SUMMARY OF THE INVENTION

The invention is directed to the development of various enzyme mutants having high relative hydrolyzing activities for elastin by modifying the substrate binding site of the enzyme, so as to solve the problems existing in the art. Moreover, the distinctive substrate specificities shown respectively by such enzyme mutants can develop new applications for the enzyme, such as the use in the treatment of foodstuff or feedstuff protein materials, to obtain products with different properties.

In one aspect, the invention provides several subtilisin YaB mutants obtained by modifying the substrate specificity of subtilisin YaB by protein engineering techniques.

The subtilisin YaB mutants are preferrably obtained by the alternation of the glycine residue(s) at the 124, 151 and/or 159 position(s) of wild type subtilisin YaB with other amino acid residue(s).

In another aspect, the invention provides nucleotide sequences encoding such subtilisin YaB mutants.

In another aspect, the invention provides expression vectors containing such nucleotide sequences encoding these subtilisin YaB mutants.

In another aspect, the invention provides methods for preparing the subtilisin YaB mutants of the invention.

In still another aspect, the invention provides the use of these subtilisin YaB mutants in the improvement of meat quality, the protein processing for foodstuff and feedstuff and other possible applications.

BRIEF DESCRIPTIONS OF THE DRAWINGS

FIG. 2 illustrates the alignment of the amino acid sequence of subtilisin YaB (SEQ ID NO:1) with subtilisin Carlsberg (SEQ ID NO:2), subtilisin BPN' (SEQ ID NO:3) and thermitase (SEQ ID NO:4).

DETAILED DESCRIPTIONS OF THE INVENTION

Figure 1:
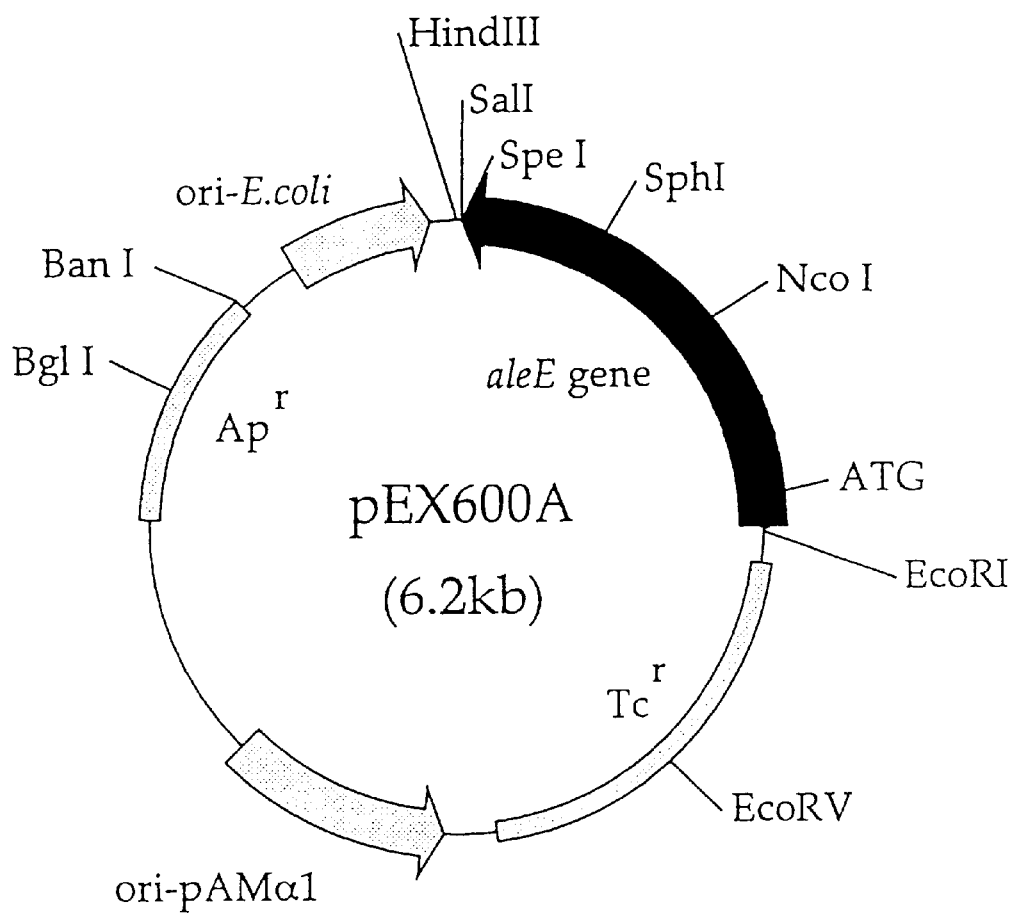
FIG. 1 shows the restriction map of plasmid pEX600 composed of pHY300PLK vector and ale gene.

The purpose of the invention is to prepare various enzyme mutants by altering the enzyme-substrate specificity of subtilisin YaB with protein engineering techniques, so as to broaden the applications of the enzyme.

In order to discuss the possibility for altering the enzyme-substrate specificity of an enzyme with unknown 3-D structure, it is necessary to first obtain the 3-D structure of the enzyme by computer modeling. Methods for modeling the 3-D structures of proteins by computer are known in the art. Preferably, modeling can be performed following standard procedures described in, for examnple, Blundell et al (1988) *Eur. J. Biochem.*, 172, 513–520; Greer (1990) *Proteins*, 7, 317–334; and Ring and Cohen (1993) *FASEB J.*, 7, 783–790, using the known 3-D structures of proteins that are highly homologous in primary structure with the subject enzyme as reference. More preferably, the reference proteins are 60% homologous in primary structure with the subject enzyme. The 3-D structure computer modeling of subtilisin YaB is performed using subtilisin BPN', subtilisin Carlsberg and thermitase as templates.

The amino acid sequence of subtilisin BPN' (SEQ ID NO:3) is 55% homologous with that of subtilisin YaB (SEQ ID NO:1) (150 out of 274 residues identical) and the amino acid sequence of subtilisin Carlsberg (SEQ ID NO:2) is 58% homologous with that of subtilisin YaB (SEQ ID NO:1) (157 out of 273 residues identical). The model of the three-dimensional structure of subtilisin YaB is constructed beginning from the structures of subtilisin BPN'-chemotrypsin inhibitor 2 and subtilisin Carlsberg-eglin complexes and is incorporated with the "deletion loop" region from the thermitase. Although thermitase is considerably different from subtilisin YaB in amino acid sequence, the secondary structure elements and overall folding of these two enzymes are very similar. Specifically, the positions of the $\alpha$-carbon atoms of these two enzyme molecules can be superimposed to within about 0.5 Å rms. Computer modeling is performed using program package QUANTA 3.2.3 (Molecular Simulations Inc., Cambridge, UK) and CHARLm 22 (Brooks et al. (1983) *J. Comput. Chem.*, 4, 187–217) running on a Silicon Graphic Crimson workstation. The coordinates of crystal structures of subtilisin BPN' in complex with chemotrypsin inhibitor 2 (PFB identification code 2SNI) (Heinz et al. (1991) *J. Mol. Biol.*, 217, 353–371), subtilisin Carlsberg in complex with eglin-C (entry 2SEC) (McPhalen et al. (1988) *Biochemistry*, 27, 6582–6598) and thermitase in complex with eglin (entry 1TEC) (Gros et al. (1989) *J. Mol. Biol.*, 210, 347–367 are available in Brookhaven Protein Data Bank (PDB).

The amino acid sequence alignment of subtilisin YaB with the above reference other subtilisin and thermitase are shown in FIG. 2. The backbone conformation of subtilisin YaB is modeled starting from appropriate segments of subtilisin BPN' and Carlsberg and the segment around the deleted region (152–162) is modeled from thermitase. Among the conserved amino acid residues of these structures, most of the side chain orientation are found to be conserved. The side chain coordinates of these residues are therefore copied directly into subtilisin YaB as an initial position. The rest of the side chain are built and adjusted one by one manually to make the packing more compact for comparison with those of known structures. There are four calcium binding sites found in this class of structures (see, Teplyakov et al. (1990) *J. Mol. Biol.*, 214, 261–279; Siezen et al. (1991) *Protein Engng.*, 4, 719–737; Gros et al. (1989) *J. Mol. Biol.*, 210, 347–367; and Heinz et al (1991) *J. Mol. Bio.*, 217, 353–371). Only the strongest binding site which appeared in subtilisin BPN' is incorporated in the model of subtilisin YaB since the coordination residues (Gln1, Asp39, Leu72, Asn74, Ile76 and Val78) are totally conserved. The initial structure is then subjected to 50 cycles of steepest descent and 200 cycles of ABNRminimization. The structure was converged rapidly without any steric clash given the proper placement of side chain conformation. A rarnachandran plot of the main chain $\phi$-$\phi$ angles in subtilisin YaB indicates that no residue is in the disallowed region. All side chain conformation analysis calculated from PROCHECK (Laskoski et al (1993) *J. Appl. Crystallogr.*, 26, 283–291) are within favorable regions. No important improvement on the model is found after the further use of molecular dynamics to minimize the structure. During the modeling process, the coordinates of eglin-C are copied directly into the structure model of subtilisin YaB since it has leucine at P1 position. Only P1' to P4 residues are used during modeling of substrate-enzyme interaction of the invention.

From the modeling of enzyme-substrate complex, the following binding pocket structures are obtained. The S1 binding pocket is a large elongated cleft with Ala149 at the entrance, Gly159 and Ala162 at the bottom and Ser126 and Ser153 at the perimeter of both sides, while Gly124 and Gly151 with the backbone of their neighboring residues form both sides of the pocket. The S2 pocket is quite narrow and shallow with the active residue His61 at the bottom, Leu93 at the side and Gly978 at the rim. The side chain of the P3 residue points away from the enzyme and the only residue with which it can interact is Ser98. The S4 pocket is bound at the bottom by Ile104 and Met132, at one side by Leu93 and Gly99, at the other side by Leu123 and Ser125 and at the rim by Ile 101. From the model of enzyme-substrate complex of the invention, both the main chain and side chain interactions between the enzyme and the substrate stabilize the substrate binding. There are five possible H-bond pairs between the enzyme and the backbone of the P1–P4 peptide, which are positioned between N of Ser214 and O of P1, O of Gly97 and N of P2, N of Gly124 and O of P3, O of Gly124 and N of P3, and N of Gly99 and O of P4, respectively.

The α-carbon of the P1 residue is used to locate suitable residues for mutation. In one embodiment, Gly124 and Gly151 are selected as the mutation sites. Gly159 residue located at the bottom of the S1 binding pocket is also selected.

To introduce mutations to given positions, it is preferably to adapt site-directed mutagenesis. Techniques for performing site-directed mutagenesis or non-random mutagenesis are known in the art. For example, variants such as the deletion, addition or substitution of residues in known amino acid sequences of proteins can be produced using known processes including alanine scanning mutagenesis (Cunningham and Wells (1989) *Science*, 244, 1081–1085), oligonucleotide-mediated mutagenesis (Adellman et al. (1983) *DNA*, 2, 183), cassette mutagenesis (Wells et al. (1985) *Gene*, 344, 315) and binding mutagenesis (Ladnerr et al., WO 88/06630).

In one embodiment of the present invention, the substitution of amino acid residue is introduced to the selected target site by oligonucleotide-mediated mutagenesis using the polymerase chain reaction technique.

Polymerase chain reaction (PCR) is one of the most commonly used techniques for amplifying specific sequences since the 1980's. See, for example, U.S. Pat. No. 4,683,195 and U.S. Pat. No. 4,683,202. The reaction is performed by first isolating the target nucleic acid sequence from a biological sample, unwinding the two strands thereof, hybridizing the unwound strands with primers synthesized according to the sequences of the two ends of the target gene, and amplifying the target gene with DNA polymerase in the presence of suitable amounts of deoxynucleoside triphosphates such as dATP, dGTP, dCTP and dTTP. The parameters and reagents required for the reaction are all well known by persons skilled in the art. Polymerase chain reaction can be performed stepwise and more commonly by commercially available automatic devices such as a thermal cycler. Additionally, the oligonucleotide sequences used as the primers for PCR can be optionally modified in part, for example, to introduce the required endonuclease restriction sites and mutations. Such oligonucleotides can be readily designed and synthesized by methods known in the art, such as that described in Crea et al. (1978) *Proc. Natl. Acad. Sci. USA*, 75, 5765.

In short, when oligonucleotide-mediated mutagenesis is utilized, target DNA is modified by the hybridization of the oligonucleotide encoding the mutation with the template DNA. The template DNA is a single-stranded plasmid or phage containing the unmodified or native DNA sequence of the target protein. After hybridization, DNA polymerase is used to synthesize the complete complementary strand of the template. The oligonucleotide primer encoding the mutation is thus incorporated into the DNA sequence of the target protein and therefore the altered code being selected is introduced. In general, oligonucleotide of at least 25 nucleotides in length is used as the primer. Preferably, the oligonucleotide has from 12 to 15 nucleotides that are fully complementary to the template in both sides of the nucleotide encoding the mutation, so as to ensure proper hybridization of the oligonucleotide with the single-stranded DNA template.

In the preferred embodiment, the ale gene encoding subtilisin YaB is carried by a suitable plasmid. More preferably, the plasmid is an expression vector, such as a plasmid from the pBR, pUC, pUB, pET or pHY4 series. The plasmid can be chosen by persons skilled in the art for convenience or as desired. For site-directed mutagenesis, the fragment containing the selected mutation site is cleaved from the ale gene encoding subtilisin YaB by restriction endonucleases as the template. Site-directed mutagenesis is carried out by a modified PCR technique (see, Higuchi et al. (1988) *Nucleic Acid Res.*, 16, 7351–7367). For each target substitution, an oligonucleotide containing the desired mutation is used as the mismatch primer to initiate chain extension between the 5' and 3 PCR flanking primers. The process includes two PCR reactions. In the first PCR, the mismatch primer and the 5' primer are used to generate a DNA fragment containing the desired base substitution. The fragment is separated from the primers by electrophoresis. After purification, it is then used as the new 5' primer in a second PCR with the 3' primer to generate the complete fragment containing the desired base substitution. After confirmation of the mutation by sequencing, the mutant fragment is then inserted back to the position of the original fragment.

Plasmids containing the wild-type ale gene and the mutant ale genes obtained by the above process are then used respectively to transform suitable host cells and expressed. Suitable host cells include bacteria such as *E. coli* or Bacillus, yeast such as *S. cerevisiae*, mammalian cells such as mouse fibroblast cell, or insect cells. Preferably, a bacterial expression system is used. Most preferably, the host is Bacillus. Protein expression is performed by processes well known in the art according to factors such as the selected host cell and the expression vector to culture the transformed host cell under conditions favorable for a high-level expression of the foreign plasmid. Such techniques have been described in details in many background references. Isolation of the protein product obtained yields crude protein extract and further purification with conventional processes such as histamine affinity chromatography or acetone precipitation gives the refined protein product.

Protease activity assays are performed to the resulting enzyme mutants with different substrate, respectively, including native substrate proteins and synthesized substrate peptides, to determine the changes in their substrate specificities. The subtilisin YaB mutants of the invention have substrate specificities that are substantially different from that of the wild type enzyme. For example, in certain embodiments of the invention, enzyme mutant 124A with a substitution at 124 position to alanine shows a high specificity for alanine and glycine and is almost completely inactive for other amino acids; enzyme mutant 151A with a substitution at 151 position to alanine shows a high specificity for alanine, glycine and leucine; and enzyme mutant 159A with a substitution at 159 position to alanine shows an enhanced reactivity for phenylalanine and leucine. Such subtilisin YaB mutants also have characteristic relative hydrolyzing activities for elastin, collagen, myofibrillar protein and casein. These enzyme mutants having special substrate specificities can develop new application possibilities for the enzyme in all application fields of proteases.

For example, the subtilisin YaB mutants of the invention can be used in the quality improvement of meat. In the art of the invention, subtilisin YaB itself is a superior meat tenderizing enzyme than other enzymes such as papain. Because the enzyme mutants provided by the invention have higher hydrolyzing activity for elastin, when used in the treatment of meat, efficacies superior than that of the wild type enzyme can be obtained.

The subtilisin YaB mutants of the invention can also be used in the processing of food proteins. It is known that when using protease to perform a low-level hydrolyzation on food proteins of soy beans, wheat and the like, followed by the treatment with other enzymes such as polysaccharide hydrolase, properties such as the foaming property, emulsifying property and nutritive property can be changed. Because the enzyme mutants of the invention have special substrate specificities, the applications thereof in this aspect can result in special effects. Special physiological activities can even be obtained from the hydorlytic production of special peptides.

The subtilisin YaB mutants of the invention can also be used in the processing of feedstuff proteins. It is known that the properties of various protein materials used in feedstuff can be changed by the treatment of proteases. Because the enzyme mutants of the invention have special substrate specificities, the applications thereof in this aspect can result in special effects. Special physiological activities can even be obtained from the hydorlytic production of special peptides.

In other possible applications of proteases, the enzyme mutants of the invention can all result in special effects because of their special substrate specificities.

Therefore, another aspect of the invention covers the new enzyme applications of the subtilisin YaB mutants of the invention, including the quality improvement of meat, the protein processing for foodstuff and feedstuff, and other possible enzyme applications.

The following examples are presented to further illustrate, but not to restrict, the preparations and the characterizations of the subtilisin YaB mutants of the invention.

Preparation of Subtilisin YaB Mutants
Site-Directed Mutagenesis

The ale gene was cloned from wild-type *B. subtilis* YaB (CCRC 11751) according to the method described in Ryuta, K., N. Koyama, Y. C. Tsai, R. Y. Juang, K. Yoda, and M. Yamasaki (1989), "Molecular cloning of the structural gene for alkaline elastase YaB, a new subtilisin produced by an alkalophilic Bacillus strain," *J. Bacteriol.*, 171:5232–5236. The ale gene for subtilisin YaB was then inserted into pHY300PLK, a shuttle vector for *E. coli* and Bacillus, to construct plasmid pEX600 (FIG. 1). The initial codon of ale was mutated from TTG to ATG. All enzymes used for gene manipulation were purchased from New England Biolabs (MA, USA) or Bethesda Research Labs (MD, USA). The conditions for gene manipulation were in accordance to the advises of the suppliers of the enzymes.

Plasmid pEX600 was digested with restriction endonuclease SphI and SpeI. The digestion products were separated by agar electrophoresis and the 491-bp fragment containing the mutation site is purified. Oligonucleotides containing the desired amino acid substitutions were synthesized respectively as primers (mismatch primers), and match primers complementary to the 3' and 5' of the above DNA fragment were also synthesized. Mutations were introduced by the modified PCR process (Higuchi et al. (1988) *Nucleic Acid Res.*, 16, 7351–7367). The above DNA fragment was used as the template. The first PCR was performed with each mismatch primer and the 5' primer to generate a DNA fragment containing the desired base substitution. The frasment obtain ed was isolated and purified by electrophoresis. The DNA fragment obtained from the first PCR was used as the new 5' primer in a second PCR with the 3' primer to generate the complete fragment containing the desired base substitution. The fragment obtained was isolated and purified by electrophoresis and sequencing was used to confirm the mutation. All enzymes used for gene manipulation were purchased from New England Biolabs (MA, USA) or Bethesda Research Labs (MD, USA). The conditions for gene manipulation were in accordance to the advises of the suppliers of the enzymes.

Expression of Wild-type and Mutant Subtilisin YaB

Each of the complete mutant DNA fragments obtained from the above process was inserted into the original location of the template fragment in plasmid pEX600. The conditions for gene manipulation were in accordance to the advises of the suppliers of the enzymes. Plasmids containing the wild-type and mutant ale genes were transformed respectively into *B. subtilis* DB104 (Kawamura and Doi (1984) *J. Bacteriol.*, 160, 422–444) by protoplast transformation as described in Chang and Cohen (1979) *Mol. Gen. Genet.*, 168, 111–115.

Transformants harboring each plasmid were isolated and then cultivated in 2×SG medium (1.5% nutrient broth, 0.1% glucose, 0.2% KCl, 0.05% $MgSO_4.7H_2O$, 1 mM Ca $(NO_3)_2$, 0.1 mM MnCl The wild-type and mutant subtilisin YaB proteins were purified from the culture broth as described in Tsai et al. (1983) *Biochem. Int.*, 7, 577–583 with some modifications. All operations were carried out at 4° C. The culture broth was precipitated by 80% saturation of ammonium sulfate. The resulting precipitate was dissolved in a minimal volume of buffer A (pH 8.0, 50 mM Tris buffer containing 1 mM $CaCl_2$) and dialyzed through a Fractogel DEAE650 column (2.5×10 cm) equilibrated with buffer A. The flow-through fraction was applied to a Sephadex C50 column (1.0×10 cm) equilibrated with buffer A. After washing with buffer A, the enzyme was eluted with a 500 ml linear gradient from 0 to 100 mM NaCl in buffer A. The active fractions were pooled, dialyzed against buffer A and then stored at –80° C.

With the above process, enzyme mutants produced by the substitution of Gly159 by an amino acid selected from the group consisting of alanine, serine, valine, isoleucine, leucine, tryptophan, tyrosine and phenylalanine, and by the substitution of Gly124 or Gly151 by an amino acid selected from the group consisting of alanine, valine, isoleucine and leucine were obtained respectively, referred to hereinafter as 159A, 159S, 159V, 159I, 159L, 159W, 159Y, 159F, 214A, 124V, 214I, 124L, 151A, 151V, 151I and 151L. In addition, double-mutation enzymes produced by the substitutions of both Gly 124 and Gly159, wherein Gly124 being substituted by alanine or serine and Gly159 being substituted by alanine or valine were also obtained, referred to hereinafter as 4A9A, 4A9S, 4V9A and 4V9S.

Substrate Specificity Assays

In comparison with the wild-type enzyme, the substrate specificities of the enzyme mutants obtained from the above process were all substantially changed. The following three types of substrates were used to evaluate the substrate specificities of the enzyme mutants.

Hydrolyzing Activity for Elastin-orcein, Casein and Myofibrilar Protein

Elastolytic activity was determined using elastin-orcein by the method described in Tsai et al. (1983) *Biochem. Int.*, 7, 577–583 with some modifications. Each enzyme obtained was shaken with 10 mg of elastin-orcein (Sigma Chemical, Co, USA) in 0.5 ml of buffer B (50 mM, pH 10.5, carbonate buffer) for 1 hour at 37° C. To stop the reaction, 1 ml of 0.7 M phosphate buffer (pH 6.0) was added. The excess substrate was removed by centrifugation and the absorbance of the supernatant was measured at 590 nm. The amount of enzyme which gave half of the absorbance at 590 nm when 10 mg of elastin-orcein was completely hydrolyzed was defined as 5 units.

Caseinolytic activity was then assayed. Each enzyme obtained was incubated with 0.5 ml of 1% casein (Merck Darmstadt, Germany) in buffer B for 10 min at 37° C. The reaction was stopped by adding 1 ml of TCA solution (0.11 M trichloroacetic acid, 0.22 M $CH_3COONa$, 0.33 M $CH_3COOH$). Following a 30-min incubation at 30° C., the precipitate was removed by centrifugation and the absorbance of the supernatant was measured at 275 nm. Units of caseinolytic activity was expressed as mg of tyrosine released per minute.

The hydrolyzing activity for myofibrillar protein was assayed by the same process as the caseinolytic activity assay. Myofibrillar protein was prepared according to the method described in Kimura and Maruyama (1983) *J. Biochem.*, 94, 283–2085. Each enzyme obtained was incubated with 10 mg myofibrillar protein substrate in 0.5 ml of buffer B for 10 min at 37° C. The reaction was stopped by adding 1 ml of TCA solution. Following a 30-min incubation at 30° C., the precipitate was removed by centrifugation and the absorbance of the supernatant was measured at 590 nm. One unit of proteolytic activity was defined as one mg of tyrosine released per minute.

Table I lists the specific hydrolyzing activities of each enzyme mutant for elastin-orcein, casein and myofibrilar protein, and the relative ratios thereof. With respect to the enzyme mutants obtained by the substitutions of Gly 124 or Gly 151 to other amino acids, except for enzyme 124A which exhibits a specific hydrolyzing activity for elastin-orcein of more than 20%, all of the other enzymes have substantially decreased specific hydrolyzing activities for elastin-orcein. However, relatively, the specific hydrolyzing activities of these enzyme mutants for casein and myofibrilar protein decrease even more dramatically. Therefore, the relative E/C ratios and the relative E/M ratios of these enzyme mutants are higher than those of wild-type enzyme.

With respect to the enzyme mutants obtained by the substitutions of Gly159 to other amino acids, the specific hydrolyzing activities of 159A and 159S for elastin-orcein increase 3.8- and 2.8-fold, respectively. The hydrolyzing activities thereof for casein and myofibrilar protein are also slightly decreased. Therefore, the relative E/C ratios of 159A and 159S increase to 4.1 and 2.6, respectively, and the relative E/M ratios thereof increase to 9.5 and 6.2. The specific hydrolyzing activities of other enzyme mutants (159V, 159Z, 159L, 159W, 159Y, 159F) are all dramatically decreased.

The four double-mutation enzymes combine the advantages of both the mutations at Gly124 and Gly159. For example, the relative E/C ratio of 4A9A is up to 4.4 and the specific hydrolyzing activity thereof is higher than the single-mutation enzyme 124A because of the introduction of the additional mutation of 159A. 4A4S, as 4A9A, also has high relative E/C ratio, relative E/M ratio and specific hydrolyzing activity. 4V9A and 4V9S are inferior than 4A9A and 4A9S in relative E/C ratio, relative E/M ratio and specific hydrolyzing activity.

From the results shown in Table I, it can be concluded that the mutations at positions 124, 151 and 159 can dramatically change the substrate specificity of the enzyme and increase its hydrolyzing activity for elastin-orcein. Among the enzyme mutants, 124A, 151A, 159A, 159S, and 4A9A and 4A9S have the most noticeable properties and applicability.

TABLE I

Hydrolysis of elastin-orcein, casein and myofibrillar proteins by wild-type and mutant subtilisin YaB

| Enzyme | Specific activity (unit/mg protein)[a] | | | Relative E/C ratio[b] | Relative E/M ratio[b] |
| --- | --- | --- | --- | --- | --- |
| | elastin-orcein | casein | myofibril | | |
| wild type | 541 (1.0) | 8250 (1.0) | 5160 (1.0) | 1.0 | 1.0 |
| G124A | 647 (1.2) | 3800 (0.46) | 1020 (0.20) | 2.6 | 6.0 |
| G124V | 425 (0.79) | 1400 (0.17) | 605 (0.13) | 4.6 | 6.7 |
| G124I | 64 (0.12) | 602 (0.073) | 717 (0.14) | 1.6 | 0.9 |
| G124L | 157 (0.29) | 1250 (0.15) | 366 (0.07) | 1.9 | 4.1 |
| G151A | 355 (0.67) | 1780 (0.22) | 750 (0.15) | 3.0 | 4.5 |
| G151V | 148 (0.27) | 618 (0.075) | — | 3.6 | — |
| G151I | 138 (0.26) | 511 (0.062) | — | 4.1 | — |
| G159L | 161 (0.30) | 717 (0.087) | — | 3.4 | — |
| G159A | 2082 (3.8) | 7780 (0.94) | 2040 (0.40) | 4.1 | 9.5 |
| G159S | 1506 (2.8) | 8940 (0.72) | 2330 (0.45) | 2.6 | 6.2 |
| G159W | 324 (0.60) | 1630 (0.20) | 672 (0.13) | 3.0 | 4.6 |
| G159V | 37 (0.068) | 431 (0.052) | — | 1.3 | — |
| G159I | 142 (0.26) | 872 (0.11) | — | 2.4 | — |
| G159L | 9 (0.017) | 112 (0.014) | — | 12 | — |
| G159F | 12 (0.022) | 135 (0.016) | — | 1.3 | — |
| G159Y | 203 (0.38) | 1010 (0.12) | — | 3.0 | — |
| 4A9A | 898 (1.7) | 3140 (0.38) | 1170 (0.23) | 4.4 | 7.3 |
| 4A9S | 554 (1.0) | 2260 (0.27) | 873 (0.16) | 3.8 | 6.1 |
| 4V9A | 552 (1.0) | 3770 (0.46) | 932 (0.18) | 1.8 | 5.6 |
| 4V9S | 79 (0.15) | 1110 (0.14) | 270 (0.052) | 1.0 | 2.8 |

[a]Values in the parentheses represent the relative specific activity or taking the specific activity of wild type for each substrate as 1.0.
[b]Relative E/C or E/M ratio is calculated by taking the relative specific activity of elastin-orcein against casein or myofibrillar protein of wild type enzyme as 1.0.

Specificity for p-nitrophenyl Ester Substrates

Esterase activities of the enzyme mutants for p-nitrophenyl ester substrates were determined at 30° C. in 50 mM Tris-HCl buffer (pH 8.0) containing 23% acetonitril. The same assay was also performed with wile-type subtilisin YaB and subtilisin BPN' (Sigma Chemical, MO, USA) for comparison. The amount of nitrophenol released was determined by measuring the absorbance at 400 nm.

The results of these assays are shown in Table II, indicating that there are substantial changes in the substrate specificities of the enzyme mutants. With respect to the enzyme mutants obtained by the substitutions of Gly124 to other amino acids, 124A and 124V react exclusively with Ala and Gly esters. For the Tyr, Phe, Leu and Val esters that can be hydrolyzed by the wild-type enzyme, the enzyme mutants are totally inactive. With respect to the enzyme mutants obtained by the substitutions of Gly151 to other amino acids, in addition to the Ala and Gly esters, 151A can also react with the Leu ester and the reactivity is up to 50% of that for Ala. However, 151A is totally inactive for the Tyr and Phe esters.

The effects of the mutations on Gly 159 are again different from those of the mutations on Gly 124 or Glyl151. Enzyme mutants 159A and 159S have dramatically increased reactivity for the Phe and Leu esters and slightly decreased reactivity for the Tyr and Gly esters.

With respect to the four double-mutation enzymes, the mutations on position 124 have stronger influences to the substrate specificity than the mutations on position 159. In other words, the double-mutation enzymes such a s 4A9A have the substrate specificities identical with those of the enzyme mutants exhibiting a single mutation on position 124, and are reactive exclusively with the Ala and Gly esters. However, the enzymatic activities of these mutants ar3le substantially increased bec ause of the introduction of the additional mutation such as 159A.

From the results shown in Table II, it can be concluded that when a group larger than methyl is introduced to position 124, the enzyme becomes inactive for substrates larger than Ala because of steric hindrance. The mutations at position 151 have the same effect, except that 151A can also react with Leu. When the Gly159 at the bottom of the substrate binding site is replaced with Ala, hydrophobic binding between the residue and the side chains of some of the substrate amino acids such as Phe can be enhanced because of steric complement and therefore, the reactivity of the enzyme for these substrates can be increased.

The $k_{cat}$ and $K_m$ values obtained are shown in Table III. The standard errors for all values reported are less than 10%. From these values, it is shown that when Gly 124 and/or Gly 151 is/are mutated to Ala or Val, the enzyme mutants obtained (including 124A, 124V, 151A, 4A9A, 4A9S and 4A9A) have decreased reactivities for sAAPFpNA and therefore the correct $k_{cat}$ and $K_m$ values cannot be obtained. 159A and 159S, on the other hand, have increased reactivities for sAAPFpNA. For example, 159A has an increase in $k_{cat}$ of about 2-fold and a substantially decrease in $K_m$, and therefore results in an increase in the $k_{cat}/K_m$ value of nearly

TABLE II

Hydrolysis of p-nitrophenyl esters by wile-type and mutant subtilisin YaB

Relative activity (%)[a]

| | Subtilisin YaB | | | | | | | | | | | Subtilisin BPN |
|---|---|---|---|---|---|---|---|---|---|---|---|---|
| Substrate | wild type | G124A | G124V | G151A | G159A | G159S | G159W | 4A9A | 4A9S | 4V9A | 4V9S | |
| Z-L-Ala-O-p-φ NO$_2$ | 100 | 61 | 77 | 41 | 42 | 52 | 37 | 155 | 114 | 92 | 29 | 45 |
| Z-L-Gly-O-p-φ NO$_2$ | 40 | 38 | 22 | 14 | 12 | 22 | 36 | 35 | 16 | 39 | 13 | 21 |
| Z-L-Val-O-p-φ NO$_2$ | 4 | 0 | 0 | 0 | 0.4 | 1 | 3 | 3 | 1 | 1 | 0 | 0.9 |
| Z-L-Leu-O-p-φ NO$_2$ | 16 | 0 | 0 | 21 | 13 | 11 | 0 | 0 | 0 | 0 | 0 | 24 |
| Z-L-Ile-O-p-φ NO$_2$ | 0 | 0 | 0 | 0 | 0 | 0 | 0 | 0 | 0 | 0 | 0 | 0 |
| Z-L-Phe-O-p-φ NO$_2$ | 14 | 0 | 0 | 0 | 30 | 35 | 3 | 3 | 1 | 0.9 | 0.3 | 25 |
| Z-L-Tyr-O-p-φ NO$_2$ | 32 | 0 | 0 | 0 | 0 | 1 | 0 | 0 | 0 | 0 | 0 | 62 |
| Z-L-Pro-O-p-φ NO$_2$ | 0 | 0 | 0 | 0 | 7 | 7 | 2 | 2 | 1 | 0.9 | 0.3 | 2.4 |
| Z-L-Arg-O-p-φ NO$_2$ | 0 | 0 | 0 | 0 | 0 | 0 | 0 | 0 | 0 | 0 | 0 | 1.4 |

[a]Data are expressed as a ratio of specific activity (A$_{400}$/mg protein)

Substrate Specificity for Synthetic Peptide Substrates

Amidase activities of the enzyme mutants were determined at 30° C. in buffer B containing 10% of N,N-dimethylformamide using succinyl-Ala-Ala-Val-Ala-p-nitroanilide (sAAVApNA) (SEQ ID NO:5) (Sigma Chemical, MO, USA), succinyl-Ala-Ala-Pro-Ala-p-nitroanilide (sAAPApNA) (SEQ ID NO:6) (Bachem, Swizerland), succinyl-Ala-Ala-Pro-Phe-p-nitroanilide (sAAPFpNA) (SEQ ID NO:8) (Sigma Chemical, MO, USA) and succinyl-Ala-Ala-Pro-Leu-p-nitroanilide (sAAPLpNA) (Sigma Chemical, MO, USA), respectively. The amount of p-nitrophenol released was measured at 410 nm ($\epsilon M=8480$ $M^{-1}cm^{-1}$). The initial reaction rate measurements were obtained at various substrate concentrations (from 0.1 mM to 2.0 mM) and the kinetic parameters, $k_{cat}$ and $K_m$, were calculated from these measurements.

10-fold. As for the reaction efficiency for sAAVApNA, except for 124V and 159A, all of the enzyme mutants have substantial increased $k_{cat}/K_m$ values resulted from the decreases of their $K_m$ values. For example, the $k_{cat}/K_m$ value of 124A increases nearly 9-fold and that of 151 A increases nearly 5-fold.

The results shown in Table III further confirm the conclusion obtained from the results shown in Table II. Namely, when a group larger than methyl is introduced to position 124 or 151, the S1 specificity of the enzyme will be limited because of steric hindrance. Because the P1 of sAAPFpNA is Phe, it cannot be hydrolyzed by enzyme mutants such as 124A and 151A.

TABLE III

Kinetic parameters for hydrolysis of synthetic peptides with wild-type and mutant subtilisin YaB Kinetic constant for

| | sAAVApNA | | | sAAPApNA | | | sAAPFpNA | | | sAAPLpNA | | |
|---|---|---|---|---|---|---|---|---|---|---|---|---|
| Enzyme | $k_{cat}$ | $K_m$ | $k_{cat}/K_m$ | $k_{cat}$ | $K_m$ | $k_{cat}/K_m$ | $k_{cat}$ | $K_m$ | $k_{cat}/K_m$ | $k_{cat}$ | $K_m$ | $k_{cat}/K_m$ |
| wild type | 3.04 | 0.214 | 14.2 | 2.04 | 1.43 | 1.67 | 24.9 | 5.41 | 4.60 | 77.4 | 14.8 | 5.25 |
| G124A | 3.52 | 0.0288 | 122 | 7.36 | 0.432 | 17.0 | ND[a] | ND | ND | ND | ND | ND |
| G124V | 1.48 | 0.228 | 6.48 | 0.787 | 1.89 | 0.416 | ND | ND | ND | ND | ND | ND |
| G151A | 1.79 | 0.0319 | 56.1 | 1.62 | 0.602 | 2.69 | ND | ND | ND | 4.27 | 0.763 | 5.59 |
| G159A | 1.89 | 0.120 | 15.7 | 1.94 | 1.87 | 1.04 | 50.3 | 1.24 | 40.5 | 17.8 | 4.60 | 3.86 |
| G159S | 2.28 | 0.116 | 19.8 | 2.90 | 1.82 | 1.60 | 20.7 | 0.58 | 35.7 | 10.2 | 2.46 | 4.13 |
| 4A9A | 3.64 | 0.0746 | 48.9 | 3.01 | 0.892 | 3.38 | ND | ND | ND | ND | ND | ND |
| 4A9S | 2.63 | 0.155 | 33.9 | 2.32 | 1.02 | 2.29 | ND | ND | ND | 0.320 | 2.49 | 0.129 |
| 4V9A | 3.32 | 0.0216 | 154 | 6.21 | 0.191 | 32.5 | ND | ND | ND | 0.300 | 1.06 | 0.282 |
| 4V9S | 0.849 | 0.0152 | 56.0 | 1.64 | 0.159 | 10.4 | ND | ND | ND | 0.0729 | 0.5354 | 0.136 |

[a]Not determined since individual $k_{cat}$ and $K_m$ values could not be determined.

The principles, preferred embodiments and formats of the invention have been described in the above paragraphs. However, it cannot be regarded that the protection scope of the invention is only limited to the specific embodiments disclosed herein. These embodiments are provided for illustration rather than restriction. Persons skilled in the art can make obvious derivations and modifications to the invention without leaving the spirit of the invention.

---

We claim:

1. A mutant subtilisin YaB obtained by one or more substitutions replacing one or more of the glycines of subtilisin YaB (SEQ ID NO: 1) produced by alkalophilic Bacillus YaB, which is selected from the group consisting of:

the mutant wherein the glycine at position 124 is substituted with alanine; the mutant wherein the glycine at position 151 is substituted with alanine; the mutant wherein the glycine at position 159 is substituted with alanine; the mutant wherein the glycine at position 159 is substituted with valine; the mutant wherein the glycine at position 124 is substituted with alanine and the glycine at position 159 is substituted with alanine; and the mutant wherein the glycine at position 124 is substituted with alanine and the glycine at position 159 is substituted with valine.

2. A nucleic acid sequence encoding the mutant subtilisin YaB of claim 1.

3. A method for improving meat quality, comprising treating meat with the mutant subtilisin YaB of claim 1.

4. A method for processing a food protein or feedstuff protein, comprising treating the food protein or feedstuff-protein with the mutant subtilisin YaB of claim 1.

* * * * *

SEQUENCE LISTING

```
<160> NUMBER OF SEQ ID NOS: 8

<210> SEQ ID NO 1
<211> LENGTH: 268
<212> TYPE: PRT
<213> ORGANISM: Bacillus subtilis

<400> SEQUENCE: 1

Gln Thr Val Pro Trp Gly Ile Asn Arg Val Gln Ala Pro Ile Ala Gln
 1               5                  10                  15

Ser Arg Gly Phe Thr Gly Thr Gly Val Arg Val Ala Val Leu Asp Thr
                20                  25                  30

Gly Ile Ser Asn His Ala Asp Leu Arg Ile Arg Gly Gly Ala Ser Phe
            35                  40                  45

Val Pro Gly Glu Pro Asn Ile Ser Asp Gly Asn Gly His Gly Thr Gln
     50                  55                  60

Val Ala Gly Thr Ile Ala Ala Leu Asn Asn Ser Ile Gly Val Leu Gly
 65                  70                  75                  80

Val Ala Pro Asn Val Asp Leu Tyr Gly Val Lys Val Leu Gly Ala Ser
                85                  90                  95

Gly Ser Gly Ser Ile Ser Gly Ile Ala Gln Gly Leu Gln Trp Ala Ala
                100                 105                 110

Asn Asn Gly Met His Ile Ala Asn Asn Ser Leu Gly Ser Ser Ala Gly
            115                 120                 125

Ser Ala Thr Met Glu Gln Ala Val Asn Gln Ala Thr Ala Ser Gly Val
    130                 135                 140

Leu Val Val Ala Ala Ser Gly Asn Ser Gly Ala Gly Asn Val Gly Phe
145                 150                 155                 160

Thr Ala Arg Tyr Ala Asn Ala Met Ala Val Gly Ala Thr Asp Gln Asn
                165                 170                 175

Asn Asn Arg Ala Thr Phe Ser Gln Tyr Gly Ala Gly Leu Asp Ile Val
            180                 185                 190

Ala Pro Gly Val Gly Val Gln Ser Thr Val Pro Gly Asn Gly Tyr Ala
        195                 200                 205

Ser Phe Asn Gly Thr Ser Met Ala Thr Pro His Val Ala Gly Val Ala
    210                 215                 220

Ala Leu Val Lys Gln Lys Asn Pro Ser Trp Ser Asn Val Gln Ile Arg
225                 230                 235                 240

Asn His Leu Lys Asn Thr Ala Thr Asn Leu Gly Asn Thr Thr Gln Phe
                245                 250                 255

Gly Ser Gly Leu Val Asn Ala Glu Ala Ala Thr Arg
            260                 265

<210> SEQ ID NO 2
<211> LENGTH: 274
<212> TYPE: PRT
<213> ORGANISM: Bacillus subtilis

<400> SEQUENCE: 2

Ala Gln Thr Val Pro Tyr Gly Ile Pro Leu Ile Lys Ala Asp Lys Val
 1               5                  10                  15
```

```
Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln

<210> SEQ ID NO 3
<211> LENGTH: 275
<212> TYPE: PRT
<213> ORGANISM: Bacillus subtilis

<400> SEQUENCE: 3

Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110
```

```
Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
        130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Gln Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
    275

<210> SEQ ID NO 4
<211> LENGTH: 279
<212> TYPE: PRT
<213> ORGANISM: Bacillus subtilis

<400> SEQUENCE: 4

Tyr Thr Pro Asn Asp Pro Tyr Phe Ser Arg Gln Tyr Gly Pro Gln
1               5                   10                  15

Lys Ile Gln Ala Pro Gln Ala Trp Asp Ile Ala Glu Gly Ser Gly Ala
                20                  25                  30

Lys Ile Ala Ile Val Asp Thr Gly Val Gln Ser Asn His Pro Asp Leu
            35                  40                  45

Ala Gly Lys Val Val Gly Gly Trp Asp Phe Val Asp Asn Asp Ser Thr
        50                  55                  60

Pro Gln Asn Gly Asn Gly His Gly Thr His Cys Ala Gly Ile Ala Ala
65                  70                  75                  80

Ala Val Thr Asn Asn Ser Thr Gly Ile Ala Gly Thr Ala Pro Lys Ala
                85                  90                  95

Ser Ile Leu Ala Val Arg Val Leu Asp Asn Ser Gly Ser Gly Thr Trp
            100                 105                 110

Thr Ala Val Ala Asn Gly Ile Thr Tyr Ala Ala Asp Gln Gly Ala Lys
        115                 120                 125

Val Ile Ser Leu Ser Leu Gly Gly Thr Val Gly Asn Ser Gly Leu Gln
    130                 135                 140

Gln Ala Val Asn Tyr Ala Trp Asn Lys Gly Ser Val Val Val Ala Ala
145                 150                 155                 160

Ala Gly Asn Ala Gly Asn Thr Ala Pro Asn Tyr Pro Ala Tyr Tyr Ser
                165                 170                 175

Asn Ala Ile Ala Val Ala Ser Thr Asp Gln Asn Asp Asn Lys Ser Ser
            180                 185                 190

Phe Ser Thr Tyr Gly Ser Val Val Asp Val Ala Ala Pro Gly Ser Trp
        195                 200                 205
```

```
Ile Tyr Ser Thr Tyr Pro Thr Ser Thr Tyr Ala Ser Leu Ser Gly Thr
    210                 215                 220

Ser Met Ala Thr Pro His Val Ala Gly Val Ala Gly Leu Leu Ala Ser
225                 230                 235                 240

Gln Gly Arg Ser Ala Ser Asn Ile Arg Ala Ile Glu Asn Thr Ala
                245                 250                 255

Asp Lys Ile Ser Gly Thr Gly Thr Tyr Trp Ala Lys Gly Arg Val Asn
            260                 265                 270

Ala Tyr Lys Ala Val Gln Tyr
        275

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: SITE
<222> LOCATION: (1)
<223> OTHER INFORMATION: Xaa= succinyl-alanine
<220> FEATURE:
<221> NAME/KEY: SITE
<222> LOCATION: (4)
<223> OTHER INFORMATION: Xaa= alanine-p-nitroanilide

<400> SEQUENCE: 5

Xaa Ala Val Xaa
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: SITE
<222> LOCATION: (1)
<223> OTHER INFORMATION: Xaa= succinyl-alanine
<220> FEATURE:
<221> NAME/KEY: SITE
<222> LOCATION: (4)
<223> OTHER INFORMATION: Xaa= alanine-p-nitroanilide

<400> SEQUENCE: 6

Xaa Ala Pro Xaa
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: SITE
<222> LOCATION: (1)
<223> OTHER INFORMATION: Xaa= succinyl-alanine
<220> FEATURE:
<221> NAME/KEY: SITE
<222> LOCATION: (4)
<223> OTHER INFORMATION: Xaa= phenylalanine-p-nitroanilide

<400> SEQUENCE: 7

Xaa Ala Pro Xaa
  1
```

```
<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptide
<220> FEATURE:
<221> NAME/KEY: SITE
<222> LOCATION: (1)
<223> OTHER INFORMATION: Xaa= succinyl-alanine
<220> FEATURE:
<221> NAME/KEY: SITE
<222> LOCATION: (4)
<223> OTHER INFORMATION: Xaa= leucine-p-nitroanilide

<400> SEQUENCE: 8

Xaa Ala Pro Xaa
```